(12) United States Patent
Peeters et al.

(10) Patent No.: US 9,267,109 B2
(45) Date of Patent: Feb. 23, 2016

(54) PATTERNED CELL SHEETS AND A METHOD FOR PRODUCTION OF THE SAME

(75) Inventors: Emiel Peeters, Eindhoven (NL); Roel Penterman, Eindhoven (NL); Ralph Kurt, Eindhoven (NL); Dirk Jan Wilfred Broer, Geldrop (NL)

(73) Assignee: Koninklijke Philips N.V., Eindhoven (NL)

( * ) Notice: Subject to any disclaimer, the term of this patent is extended or adjusted under 35 U.S.C. 154(b) by 1070 days.

(21) Appl. No.: 12/746,767

(22) PCT Filed: Dec. 5, 2008

(86) PCT No.: PCT/IB2008/055115
§ 371 (c)(1),
(2), (4) Date: Jun. 8, 2010

(87) PCT Pub. No.: WO2009/074932
PCT Pub. Date: Jun. 18, 2009

(65) Prior Publication Data
US 2010/0261270 A1  Oct. 14, 2010

(30) Foreign Application Priority Data
Dec. 10, 2007 (EP) ..................................... 07122703

(51) Int. Cl.
*C12N 5/00* (2006.01)

(52) U.S. Cl.
CPC .......... *C12N 5/0068* (2013.01); *C12N 2535/10* (2013.01); *C12N 2539/10* (2013.01)

(58) Field of Classification Search
CPC .......... C12N 2535/10; C12N 2539/10; C12N 5/0068
See application file for complete search history.

(56) References Cited

U.S. PATENT DOCUMENTS

| 5,324,591 | A | * | 6/1994 | Georger et al. ................ 428/552 |
| 5,512,131 | A | | 4/1996 | Kumar et al. |
| 5,935,593 | A | * | 8/1999 | Ron et al. ...................... 424/423 |
| 6,939,378 | B2 | | 9/2005 | Fishman et al. |
| 7,267,982 | B2 | | 9/2007 | Tsuzuki et al. |
| 7,405,078 | B2 | | 7/2008 | Okano et al. |

| 2003/0047535 | A1 | | 3/2003 | Schueller et al. |
| 2003/0219889 | A1 | * | 11/2003 | Sumaru et al. ............. 435/287.1 |
| 2007/0015153 | A1 | | 1/2007 | Amontov et al. |
| 2007/0087114 | A1 | | 4/2007 | Chilkoti et al. |

FOREIGN PATENT DOCUMENTS

| JP | 2003028170 A | 1/2003 |
| JP | 2006008975 A | 1/2006 |
| WO | 2005045524 A2 | 5/2005 |
| WO | 2006117745 A2 | 11/2006 |
| WO | 2007063736 A1 | 6/2007 |

OTHER PUBLICATIONS

Matsuda et al. Tissue Engineering Based on Cell Sheet Technology. Adv. Mater. 2007, 19, 3089-3099.*
Alarcon et al. Stimuli responsive polymers for biomedical applications. Chem. Soc. Rev., 2005, 34, 276-285.*
Whitesides et al: "Soft Lithography in Biology and Biochemistry" Annu. Rev. Biomed. Engineering, 2000, vol. 3, pp. 335-373.
Kikuchi et al: "Nanostructured Designs of Biomedical Materials: Applications of Cell Sheet Engineering to Functional Regenerative Tissues and Organs"; Journal of Controlled Release, 2005, vol. 101, pp. 69-84.
Leclere et al: "In Situ Micropatterning Technique by Cell Crushing for Co-Cultures Inside Microfluidic Biochips"; Biomed Microdevices, 2008, vol. 10, pp. 169-177.
Y. Tsuda et al., "The Use of Patterned Dual Thermoresponsive Surfaces for the Collective Recovery as Co-Cultured Cell Sheets", Biomaterials, 2005, May; 26(14): 1885-1893.
Qiu et al.,"Environment-sensitive Hydrogels for Drug Delivery", Advanced Drug Delivery Reviews, vol. 53, Aug. 2001, pp. 321-339.
Bartil, T. et al., "Swelling Behavior and Release Properties of pH-sensitive Hydrogels Based on Methacrylic Derivatives", Acta Pharmaceutica, vol. 57, No. 3, Sep. 2007, pp. 301-314.

* cited by examiner

*Primary Examiner* — Taeyoon Kim (57) ABSTRACT

The present invention is related to a method for the production of cell sheets comprising at least two different cell types, said method comprising the steps of providing a continuous cell sheet which is disposed on a substrate comprising shape transition properties and/or alterable surface characteristics; exposing said continuous cell sheet to a releasing agent in a patterned fashion; washing the cell sheet after exposure to the releasing agent in order to remove cells which have been affected by the releasing agent, and repopulating the gaps remaining after the cells which have been affected by the releasing agent have been removed with a second cell type.

7 Claims, 4 Drawing Sheets

PATTERNED CELL SHEETS AND A METHOD FOR PRODUCTION OF THE SAME

BACKGROUND OF THE INVENTION

This invention relates to a the field of tissue engineering. More specifically, the invention relates to patterned cell sheets and to a method for their production.

Regenerative medicine is a new upcoming discipline within the field of medical sciences. There are numerous methods and approaches used in regenerative medicine. They can coarsely be divided into four areas, including tissue engineering in vitro and in vivo:

In tissue engineering in vitro, tissue is grown outside the body utilising scaffolds and cells. The engineered tissue is subsequently implanted in a patient in order to replace damaged or lost tissue.

In tissue engineering in vivo, scaffolds are placed in damaged tissue areas with the aim of inducing growth of cells from the surrounding healthy tissue to restore damaged tissue.

However, the use of scaffold suffers from many disadvantages and short-comings. In specific applications, cell sheet engineering can avoid the limitations of scaffold based tissue reconstruction and cell therapies. Cell sheets have been used for the reconstruction of ocular surface tissue, periodontal ligaments, cardiac patches and bladder augmentation. For more complex applications it is required that cells are placed in specific locations or predetermined patterns, hence patterned cell-sheets are desired. For the reconstruction of even more complex tissues, the use of heterogeneous multicellular sheets is needed. For this purpose different cell types have to be co-cultured in a patterned fashion in order to obtain a cell sheet in which the different cell types are micro-patterned in a desired pattern.

State of the art methodologies to obtain patterned cell sheets are based upon patterning the surface on which the cells are cultured. These methodologies require that each substrate is patterned separately using (soft)lithography. Furthermore these methodologies do not facilitate the production of freestanding patterned cell sheets.

BACKGROUND ART

In U.S. Pat. No. 6,939,378 a method for the treatment of membranous tissue is disclosed, which provides deposition of proteolytic enzymes onto the membranous tissue effective to biologically etch the surface and interior of the membranous tissue to provide desired topology and surface adhesion properties to the tissue.

However, the release of the cell sheet thus produced can be cumbersome, as the remaining cells are tightly attached to the substrate by means of extracellular matrix proteins, like collagen and, among others, fibrin, elastin, fibronectins, laminins, nidogen and integrins, as well as due to mere adhesive and electrostatic forces.

In Tsuda et al., Biomaterials 26 (2005), 1885-1893 freestanding heterogeneous patterned cell sheets are disclosed, as well as a method to produce such cell sheets. However, said method has some severe drawbacks, as, among others, (i) it involves the use of a substrate which is very complicated to make, involving multiple (patterned) electron beam irradiation steps, (ii) it only demonstrates cell sheets with two different cell types, whereas cell sheets incorporating more than two cell types are difficult to obtain with said method, and (iii) in said method one of the cell types needs to be cultured at 27° C., which is far from optimal for cell growth, cell proliferation, cell differentiation and the like.

OBJECT OF THE INVENTION

It is therefore the object of the present invention to provide a method for the production of cell sheets comprising at least two different cell types which avoids these limitations.

This object is met with method for the production of patterned cell sheets according to the independent claims. The dependent claims provide preferred embodiments.

SUMMARY OF THE INVENTION

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a", "an" and "the" include singular and/or plural referents unless the context clearly dictates otherwise. It is moreover to be understood that, in case parameter ranges are given which are delimited by numeric values, the ranges are deemed to include these limitation values.

Additional details, features, characteristics and advantages of the object of the invention are disclosed in the subclaims, the figures and the following description of the respective figure and examples, which, in an exemplary fashion, show preferred embodiments of according to the invention. However, these drawings should by no means be understood as to limit the scope of the invention.

To provide a comprehensive disclosure without unduly lengthening the specification, the applicant hereby incorporates by reference each of the patents and patent applications referenced above.

The particular combinations of elements and features in the above detailed embodiments are exemplary only; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. Furthermore, reference signs used in the description and claims do not limit the scope of the invention as claimed.

According to the invention, a method for the production of cell sheets comprising at least two different cell types is provided, said method comprising the steps of:
a) providing a continuous cell sheet which is disposed on a substrate comprising inducible shape transition properties and/or alterable surface characteristics;
b) exposing said continuous cell sheet to a releasing agent in a patterned fashion;
c) washing the cell sheet after exposure to the releasing agent in order to remove cells which have been affected by the releasing agent, and
d) repopulating the gaps remaining after the cells which have been affected by the releasing agent have been removed with a second cell type.

Surprisingly it turned out that such method avoids the drawbacks set forth above, as involved with methods according to the prior art.

Furthermore, the inventors found to their surprise that the biological etching method as described in U.S. Pat. No. 6,939,378 can as well be applied on single layer cell sheets, while the etched areas can then be repopulated with a second cell type. The method according to the invention does therefor substantially facilitate the manufacturing of freestanding heterogeneous patterned cell sheets The term "in a patterned fashion", a regular pattern, e.g. a grating, or an irregular pattern. This definition does moreover include heterogeneous patterns.

The term "substrate comprising inducible shape transition properties" as used herein, shall relate to a substrate which, upon a given stimulus, changes its shape, its volume, its water content and/or its specific density. Potential materials comprised in such substrate, and potential stimuli useful to elicit said transition, are discussed below.

The term "substrate comprising alterable surface characteristics" as used herein, shall relate to a substrate which, upon a given stimulus, changes at least one of its surface characteristics, selected from the group consisting of surface tension, surface hydrophilicity, surface net charge, surface contact angle, surface roughness and surface adhesion.

The term "releasing agent", as used herein, shall relate to an agent which supports a release of individual cells when being in contact with said agent. Therefore, adhesive connections between the respective cells and the substrate, or neighboring cells, respectively, are disrupted, detached, digested or the like, both directly and indirectly. Such adhesive connections may for example be part of the extracellular matrix, like anchorage proteins, potential releasing agents are discussed below.

In a preferred embodiment, the above method does further comprise at least one repetition of steps b)-d). Preferably, the releasing agent pattern the cell sheet is exposed to in the second (and, optionally the succeeding) cycle is preferably different for the one in the preceding cycle, e.g. the first cycle.

In yet another preferred embodiment of the present invention a method for the production of freestanding cell sheets is provided, said method comprising at least two different cell types, said method comprising, in addition to steps a)-d) as set forth in the aforementioned claims a step of e) releasing the thus obtained cell sheets by inducing a shape transition in the said substrate.

Surprisingly, it turned out that the use of a substrate comprising inducible shape transition properties and/or alterable surface characteristics solves the above mentioned problems related to the release of the cell sheet. The inventors found out that, in many cases, after a shape transition of the substrate, or an alteration of its surface characteristics, the patterned cell layer, which is often quite fragile due to the gaps produced, can easily be released from the substrate with out the additional use of a releasing agent. The thus released cell layers could easily be translocated to another substrate, and the cells turned out to be very vital, i.e. they could be used for the production of heterogeneous tissues. This is an important requirement for their use in tissue engineering.

In a preferred embodiment it is provided that the said releasing agent is a chemical agent. Such chemical releasing agent may for example be EDTA, which is known to bind bivalent cations, like $Ca^{2+}$, which is a cofactor of integrins, and which is involved in collagen synthesis. The use of EDTA alone may thus result in a disruption of the extracellular matrix and, accordingly, to a cell release. The same is applicable for EGTA, which however bind $Ca^{2+}$ preferably.

The skilled person will find from this teaching other chemical agents the application of which results in a disruption of the extracellular matrix and, accordingly, to a cell release. These embodiments are thus deemed to fall under the scope of the present invention.

Other chemical releasing agents comprise cytotoxic agents. In this case, the respective cells are rather inactivated, or killed, which leads to their disintegration, and, subsequently, to their release. This means that the adhesive connections between the respective cells and the substrate, or neighboring cells, respectively, are disrupted, detached or digested indirectly, in contrast to those treatments which lead to a direct disruption, detachment or digestion.

In yet another preferred embodiment it is provided that the said releasing agent is an enzyme. The said enzymes are preferably proteolytic enzymes, like trypsin, collagenase or pronase. These enzymes digest major part of the extracellular matrix proteins, e.g. fibronectin, but also collagen and, among others, fibrin, elastin, laminins, nidogen and integrins, and will thus lead to a cell release. Other potential enzymes are splitase, a crustacean enzyme which is useful in some applications where the above mentioned enzymes, which are often of bovine origin, can not be used due to risk of contamination (BSA, viruses and the like).

Among these enzymes, trypsin is particularly preferred due to is broad activity against all major extracellular matrix proteins, and its low impact on the activity and viability of the cells.

In a preferred embodiment, the said enzymes are used in combination with EDTA or EGTA. The addition of EDTA or EGTA leads to the above described effects. Moreover, divalent cations, (above all, $Ca^{2+}$) tend to inhibit proteases, particularly trypsin. The removal of these cations from the medium with EDTA will thus increase the activity of the said enzymes.

The skilled person will find from this teaching other enzymes the application of which results in a digestion of at least parts of the extracellular matrix and, accordingly, to a cell release. These embodiments are thus deemed to fall under the scope of the present invention.

In yet another preferred embodiment it is provided that the said releasing agent is a physical stimulus. Such physical stimulus may for example be any kind of electromagnetic or particle radiation, like laser radiation, X-Ray, alpha-, beta- or gamma-radiation. These stimuli may be brought in contact with the cell sheet by means of a scanning device, i.e. a device providing a small spot of radiation which is then scanned over the cell layer in a pattered fashion, or by means of a projection apparatus providing a patterned radiation scheme on the cell sheet, similar to the processes known from photolithography. Again, the respective cells are rather inactivated, or killed, which leads to their disintegration, and, subsequently, to their release. This means that the adhesive connections between the respective cells and the substrate, or neighboring cells, respectively, are disrupted, detached or digested indirectly, in contrast to those treatments which lead to a direct disruption, detachment or digestion.

Other physical stimuli may comprise the administration of electricity. These stimuli may be brought in contact with the cell sheet by means or a patterned electrode array, or at least one electrode which is scanned over the surface of the cell layer. In these cases, the electrical parameters are selected in such way that cells being in contact with an electrode are inactivated, or killed, which leads to their disintegration, and, subsequently, to their release. This means that the adhesive connections between the respective cells and the substrate, or neighboring cells, respectively, are disrupted, detached or digested indirectly, in contrast to those treatments which lead to a direct disruption, detachment or digestion.

Yet other physical stimuli may comprise a thermal stimulus, i.e. the administration of heat and/or chill. Such stimulus may be brought to the cells by means of a patterned stamp, e.g. a piezo element having a grated pattern on the side contacting the cells, or by at least one thermal probe which is scanned over the surface of the cell layer. The thermal parameters are selected in such way that cells being in contact with an electrode are inactivated, or killed, which leads to their disintegration, and, subsequently, to their release. This means that the adhesive connections between the respective cells and the substrate, or neighboring cells, respectively, are disrupted, detached or digested indirectly, in contrast to those treatments which lead to a direct disruption, detachment or digestion.

Still other physical stimuli may comprise the application of physical force, i.e. of pressure or a vacuum. Again, the administration has to take place in a patterned fashion, e.g. by means of a patterned stamp or a patterned vacuum element, or by means of a scanning pressure probe or a scanning vacuum element, which is scanned over the surface of the cell layer. The physical parameters are selected in such way that cells being in contact with an electrode are inactivated, or killed, which leads to their disintegration, and, subsequently, to their release. This means that the adhesive connections between the respective cells and the substrate, or neighboring cells, respectively, are disrupted, detached or digested indirectly, in contrast to those treatments which lead to a direct disruption, detachment or digestion.

Preferably, the said releasing agent is loaded on a stamp having a relief structure which corresponds to the cell pattern to be produced.

This method is especially useful when chemical or enzymatic releasing agents are used. The said relief may, in one preferred embodiment, provide patterned microcavities which take up small volumes of the releasing agent, like an enzyme or a chelator. The stamp is then brought in contact with the cell sheet, where it remains for a given period of time to bring the respective agents in contact with the cells.

In another preferred embodiment, the releasing agent (also termed "biological ink") diffuses into the stamp material in a first step (termed "inking step"), i.e. the stamp is soaked with the releasing agent, which diffuses out of the stamp material, or is squeezed out of the stamp material due to exertion of pressure, in a second step (termed "printing step") when in contact with the cell layer.

Only in the contact areas between the cell sheet and the stamp, the cells are exposed to the releasing agent, i.e. trypsin, and only in those areas the adhesive connections between the respective cells and the substrate, or neighboring cells are cleaved by the releasing agent and the cells are released from the substrate. In other words, patterned release of cells is achieved through microcontact printing of a releasing agent.

Preferably, such stamp is made from an elastomer, like Polydimethylsiloxane (PDMS). Such elastomeric stamp having patterned relief structures is produced according to standard procedures known in the art of microcontact printing.

In another preferred embodiment, the said releasing agent is administered to the cells in a patterned fashion by means of a plotter.

Again, this method is especially useful when chemical or enzymatic releasing agents are used. Such plotter can for example work similar to a bubble jet printer or a needle printer.

Furthermore, the said substrate comprising inducible shape transition properties and/or alterable surface characteristics is a hydrogel. The term "hydrogel" as used herein implies that at least a part of the respective material comprises polymers that in water form a water-swollen network and/or a network of polymer chains that are water-soluble. Preferably the hydrogel permeation layer comprises in swollen state ≥50% water and/or solvent, more preferably ≥70% and most preferred ≥80%.

A responsive hydrogel is particularly preferred. In the sense of the present invention, the term "responsive" means and/or includes especially that the hydrogel is responsive in such a way that it undergoes a change of shape and total volume upon a change of a specific parameter, or the application of a specific stimulus, the nature of which is further specified above (e.g. induced change of pH, induced change of temperature, induced exposure to electromagnetic waves, induced exposure to specific salts or organic compounds, or to a given concentration thereof, application of an electric field, application of a magnetic field, application of sound, application of vibrations). Other stimuli include the presence or concentration of dedicated analytes such as enzymes or other biomolecules. (see comment above).

Hydrogels are known to be shape sensitive to pH, ion concentration, temperature, solvent composition and/or electric potential. These parameters may cause a change in phase, shape, mechanics, refractive index, recognition or permeation rates that subsequently can be reversed to return the material to its original state.

Furthermore, these Hydrogels may undergo changes in its surface characteristics, like surface tension, surface hydrophilicity, surface net surface contact angle, surface roughness and surface adhesion, upon a change in pH, ion concentration, temperature, solvent composition and/or electric potential.

Stimuli-sensitive hydrogels have also been integrated with enzymes, protein mimics, and antibodies to design controllable actuators. These hydrogels have been shown to swell on addition of a target molecule. The amount of swelling of these hydrogels was attributed to changes in non-covalent interactions within the polymer network. The hydrogels can be also designed to swell upon presence of a target molecule; even they can be constructed in a way that the magnitude of swelling can be proportional to the concentration of ligand present.

According to an embodiment of the present invention, the hydrogel material comprises a material selected out of the group comprising poly(meth)acrylic materials, substituted vinyl materials or mixtures thereof, as well as include epoxides, oxetanes, and thiolenes.

According to another embodiment of the present invention, the hydrogel material comprises a poly(meth)acrylic material made out of the polymerization of at least one (meth)acrylic monomer and at least one polyfunctional (meth)acrylic monomer.

According to yet another embodiment of the present invention, the (meth)acrylic monomer is chosen out of the group comprising N-isopropyl(meth)acrylamide (meth)acrylamide, hydroxyethyl(meth)acrylate, ethoxyethoxyethyl (meth)acrylate or mixtures thereof.

According to still another embodiment of the present invention, the polyfunctional (meth)acrylic monomer is a bis-(meth)acryl and/or a tri-(meth)acryl and/or a tetra-(meth) acryl and/or a penta-(meth)acryl monomer.

According to an embodiment of the present invention, the polyfunctional (meth)acrylic monomer is chosen out of the group comprising bis(meth)acrylamide, diethyleneglycoldi (meth)acrylate, triethyleneglycoldi(meth)acrylate, tertraethyleneglycoldi(meth)acrylatetripropyleneglycol di(meth) acrylates, pentaerythritol tri(meth)acrylate polyethyleneglycoldi(meth)acrylate, ethoxylated bisphenol-A-di(meth)acrylate, hexanedioldi(meth)acrylate or mixtures thereof.

Other materials which turned out in tests carried out by the inventors to be suitable for the above purposes include Ethylhexyl(meth)acrylate, Hydroxyethyl(meth)acrylate, PNIPAA-co-isobutyl(meth)acrylate (80:20), PMMA, PMMA-co-trimethylolpropane triacrylate, TMPTA, DEGDA, DEGDMA, Polystyrene, PMMA-co-DEGDA (2:1), PMMA-co-DEGDMA (2:1), PS-co-TMPTA (2:1), PS-co-DEGDA (2:1), PS-co-DEGDMA (2:1) and tris 2-hydroxyethyl isocyanurate triacrylate.

According to an embodiment of the present invention, the hydrogel material comprises an anionic poly(meth)acrylic material, preferably selected out of the group comprising (meth)acrylic acids, 2-ethylacrylic acid, 2-propyl arylic acid, arylsulfonic acids, especially styrenesulfonic acid, itaconic acid, crotonic acid, sulfonamides or mixtures thereof, and/or a cationic poly(meth)acrylic material, preferably selected out of the group comprising vinyl pyridine, vinyl imidazole, aminoethyl(meth)acrylates or mixtures thereof, co-polymerized with at least one monomer selected out of the group neutral monomers, preferably selected out of the group vinyl acetate, hydroxyethyl(meth)acrylate(meth)acrylamide, ethoxyethoxyethyl(meth)acrylate or mixture thereof, or mixtures thereof.

It is known for a wide range of these co-polymers to change their shape as a function of pH and to respond to an applied electrical field and/or current. Therefore these materials may be of use for a wide range of applications within the present invention.

According to an embodiment of the present invention, the hydrogel material comprises a substituted vinyl material, preferably vinylcaprolactam and/or substituted vinylcaprolactam.

According to an embodiment of the present invention, the hydrogel material is based on thermo-responsive monomers selected out of the group comprising N-isopropylamide, diethylacrylamide, carboxyisopropylacrylamide, hydroxymethylpropylmethacrylamide, acryloylalkylpiperazine and copolymers thereof with monomers selected out of the group hydrophilic monomers, comprising hydroxyethyl(meth)acrylate, (meth)acrylic acid, acrylamide, polyethyleneglycol (meth)acrylate or mixtures thereof, and/or co-polymerized with monomers selected out of the group hydrophobic monomers, comprising (iso)butyl(meth)acrylate, methylmethacrylate, isobornyl(meth)acrylate or mixtures thereof. These co-polymers are known to be thermo-responsive and therefore may be of use for a wide range of applications within the present invention.

A preferred example for these responsive hydrogels is Poly-n-isopropylacrylamide (PNIPAA).

Furthermore, in a preferred embodiment of the method according to invention it is provided that the induction of a shape transition in the substrate comprising shape transition properties and/or the alteration of surface characteristics in the substrate comprising alterable surface characteristics comprises at least one step selected from the group consisting of
  Raising and/or lowering the temperature of the medium
  Raising and/or lowering the osmolarity of the medium
  Raising and/or lowering the pH of the medium
  Providing an electrical stimulus to the medium
  Providing an light stimulus to the medium, particularly IR or UV-light
  Magnetic field, or combinations thereof.

Furthermore, a method for the production of stacked cell sheets comprising at least two different sheets is provided, of which at least one comprises at least two least two different cell types each, said method comprising, in addition to steps a)-e) as set forth in the aforementioned claims a step of
  f) superimposing at least two cell sheets of which at least one sheet is obtained with a method as obtained according to the aforementioned claims.

The different cell types according to the above may be (i) either different cell types in a biological meaning, or (ii) they may have the same origin, wherein at least one type has undergone at least one treatment selected from the group consisting of
  enzymatic and/or pharmaceutic treatment,
  genetic manipulation treatment,
  exposure to electromagnetic radiation or particle radiation,
  exposure to heat and/or chill,
  exposure to a magnetic field,
  selection after phenotypic and/or genotypic characterization, and the like.

In yet another embodiment a cell sheet and/or stack of cell sheets produced with any of the aforementioned methods, wherein said cell sheet and/or stack of cell sheets has a patterned shape, wherein said cell sheet and/or stack of cell sheets comprises at least two different cell types and/or at least two different cell sheets.

In this embodiment, it is provided that the patterns of the at least two cell sheets are preferably adapted to one another in a complementary fashion, in order to create, when the cell layers are superimposed, a heterogeneous tissue. In this embodiment, Release step e) can take place after or before step ii). It is an option which falls under the scope of this embodiment to provide three or more patterned cell sheets, which have complementary patters, and superimpose them in order to create a tissue having three or more different cell types.

In yet another embodiment of the present invention a cell sheet and/or stack of cell sheets is provided, said cell sheet and/or stack of cell sheets comprising a patterned shape, wherein said cell sheet and/or stack of cell sheets comprises at least two different cell types and/or at least two different cell sheets Furthermore, the use of a cell sheet and/or a stacked cell sheet according to the invention for the production of ocular surface tissue, periodontal ligaments, cardiac patches, bladder tissue, two-dimensional tissues, three-dimensional tissues, bone material, skin and/or cartilage material is provided.

In another embodiment, the use of a cell sheet according the invention for the production of a stacked heterogeneous cell sheet is provided.

Furthermore, the use of a cell sheet, of a stacked cell sheet and/or of a product according to the invention to for the production of an artificial tissue and/or organ is provided Furthermore, the use of a cell sheet, of a stacked cell sheet, of a product according and/or of an artificial tissue and/or organ according to the invention for the treatment of a human or an animal is provided.

It is to be mentioned that the term "patterned shape" may for example be a grid, a lined arrangement of cells, or any pattern corresponding to a desired distribution of different cell types for the production of specific tissue types or tissue patches.

EXAMPLES

In the following, the present invention is demonstrated by means of examples, which by no means should be understood as to limit the scope of the invention.

Example 1

Figure 1A:
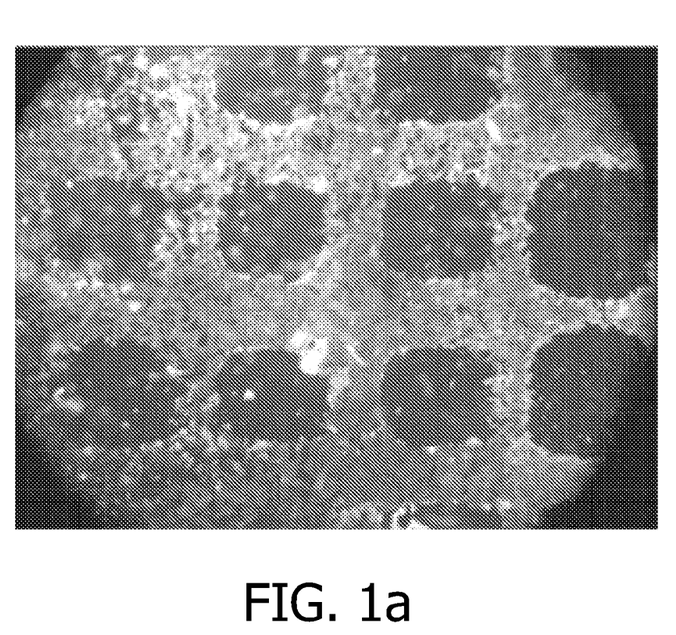
FIGS. 1a and 1b show photomicrographs of patterned cell sheets with a single cell layer.
Figure 1B:
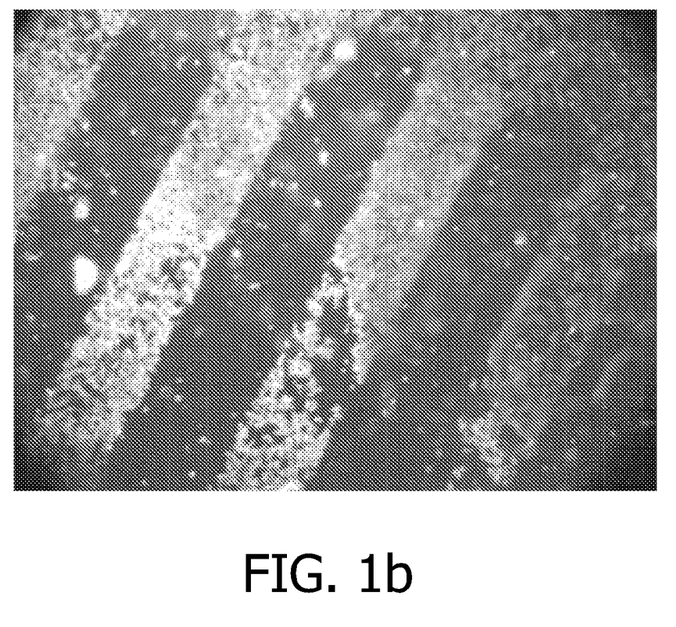

An elastomeric stamp having a patterned relief structure is partly submerged in a solution comprising trypsin as a releasing agent. 3T3 mouse fibroblast cells are cultured in a 6 wells plate using standard methods known in the art. When the cells reach >90% confluence the well plate is taken out of the the incubator and the medium is carefully pipetted from the wells. The stamp loaded with trypsin is subsequently placed on a continuous sheet of 3T3 mouse fibroblast cells. The well plate is put back in the incubator for 5 min for incubation, and thereafter the stamp is carefully removed and the cell sheet is carefully washed with PBS. The washing leads to a release of those cells which have been in contact with the releasing agent, resulting in patterned cell sheets as shown in FIG. 1, which shows cell sheets with a grid pattern (FIG. 1A) or a lined pattern (FIG. 1B). The pattern has a gap size of approximately 1 mm. Smaller patterns with gap sizes down to 50 μm can be obtained using an appropriate stamp.

Example 2

By growing the cells on a substrate comprising inducible shape transition properties and/or alterable surface characteristics it is possible to release the patterned cell sheet after the microcontact printing step by inducing a shape transition of said substrate. Such substrate may for example be an agar being coated with a thin layer of Poly(N-isopropylacrylamide) (PNIPAA). The shape transition is induced by lowering the temperature to below 32° C. At this temperature the Poly (N-isopropylacrylamide) shows a transition from the collapsed hydrophobic state to a hydrophilic swollen hydrogel state affecting the affinity of the cells to the substrate. As a result of this transition the patterned cell sheet will release from the substrate without breaking the interactions between the cells. Optionally, the patterned cell sheet may be treated with a releasing agent before the shape transition in order to facilitate the release.

The stimulus used to induce said shape transition is a thermal stimulus. At room temperature the responsive hydrogel shows strong swelling in water. In an incubator used for cell culture, however, a temperature of about 37° C. is maintained, which causes the hydrogel to collapse (PNIPAA has a lower critical solution temperature (LCST) at 33° C.).

Additional details, features, characteristics and advantages of the object of the invention are disclosed in the subclaims, the figures and the following description of the respective figure and examples, which, in an exemplary fashion, show preferred embodiments of a process and flakes according to the invention.

FIGS. 1a and 1b show photomicrographs of patterned cell sheets with a single cell layer, which form part of the freestanding cell sheets comprising at least two different cell types. Feature sizes in the photomicrographs are approximately 1 mm.

In FIG. 1a, the obtained pattern is a grid pattern. For this purpose, the stamp used for the printing step has a pattern of squares with grid-like cavities between the different squares. In FIG. 1b, the obtained pattern is a line pattern. For this purpose, the stamp used for the printing step has a pattern of lines with lined cavities in between.

Figure 2A:
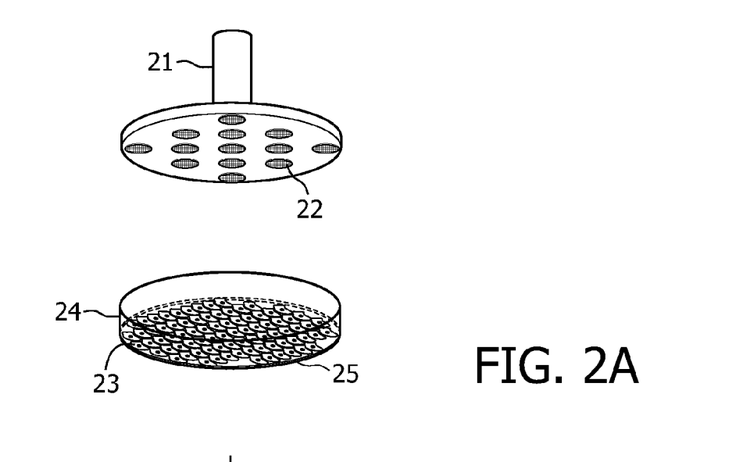
FIGS. 2A, B and C show a method for the preparation of patterned cell sheets with a single cell layer.
Figure 2B:
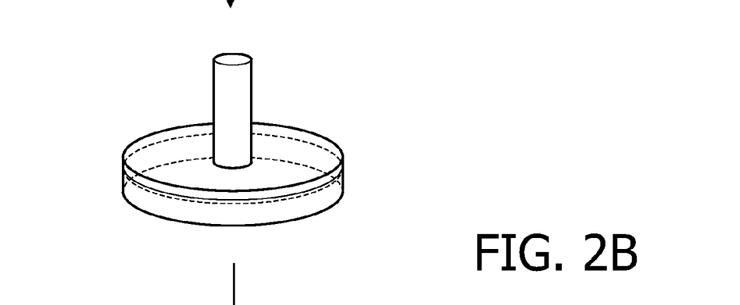
Figure 2C:
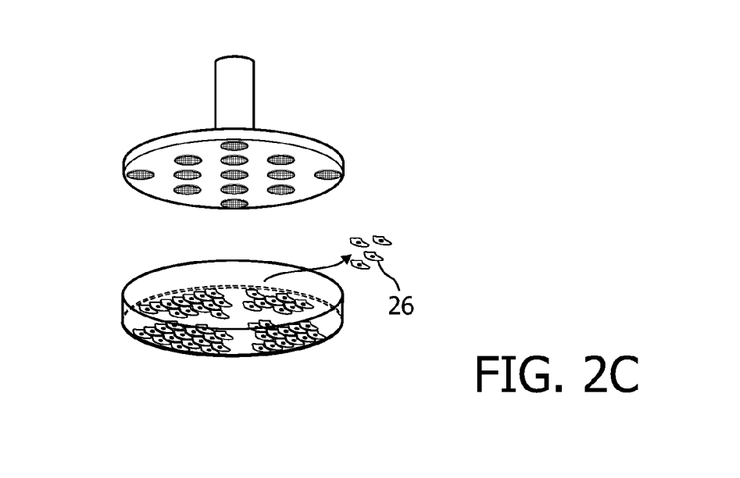

FIG. 2 shows a method for the preparation of patterned cell sheets with a single cell layer, subdivided into three substeps A ("inking step"), B ("printing step") and C ("washing step"). In step A, a stamp 21 having a relief pattern with protrusions 22 made out of elastomeric material is provided which has before been soaked with a releasing agent according to the invention ("inking step"). In step B the stamp is then disposed on a homologous cell sheet 23 which grows in a petri dish 24 on a substrate 25 comprising inducible shape transition properties and/or alterable surface characteristics. Upon contact with the cell sheet the releasing agent diffuses into the cell sheet, or is squeezed out of the stamp material due to exertion of pressure. After a given incubation time the stamp is removed, and the cells 26 which have been in contact with the releasing agent are washed out in step C. The thus produced patterned cell sheet may then be released from the substrate 25 comprising inducible shape transition properties and/or alterable surface according to the description.

Figure 3:
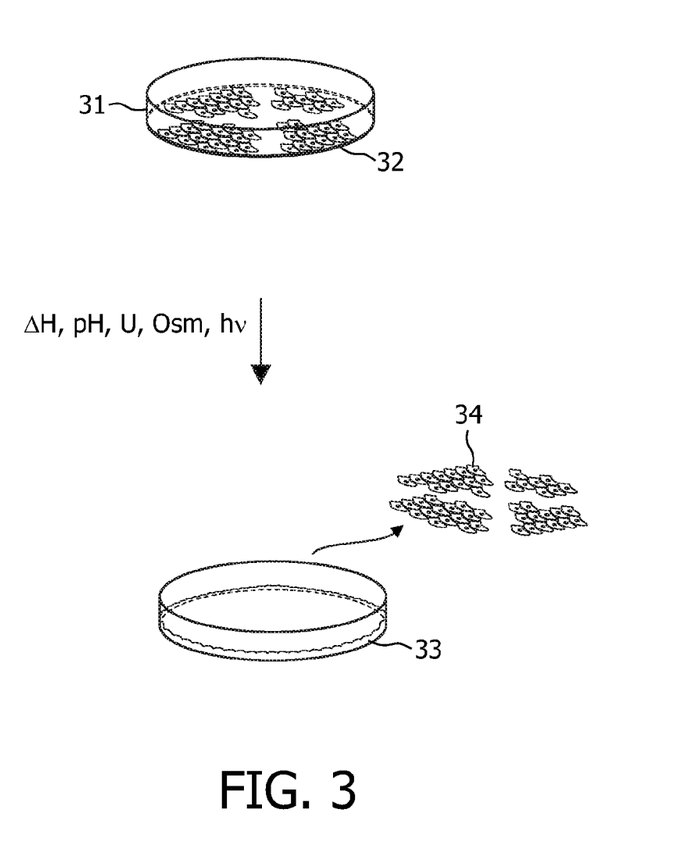
FIG. 3 shows release of a patterned cell sheet with a single cell layer.

FIG. 3 shows the release of the patterned cell sheet with a single cell layer, which grows in a petri dish 31 on a substrate 32 comprising inducible shape transition properties and/or alterable surface characteristics. A given stimulus leads to a shape transition of the substrate 33, which in turn promotes the release of the cell sheet without the additional use of a releasing agent. The thus released cell layers 34 can easily be translocated to another substrate, and the cells remain very vital, i.e. they could be used for the production of heterogeneous tissues. This is an important requirement for their use in tissue engineering. The said stimulus may, for example, be selected from the group consisting of Raising and/or lowering the temperature of the medium (ΔH)

Raising and/or lowering the osmolarity of the medium (Osm)

Raising and/or lowering the pH of the medium (pH)

an electrical stimulus to the medium (U)

a light stimulus to the medium (hν

If, for example, the said substrate consists of an agar being coated with a thin layer of Poly(N-isopropylacrylamide) (PNIPAA), the shape transition is induced by lowering the temperature to below 32° C. At this temperature the Poly(N-isopropylacrylamide) shows a transition from the collapsed hydrophobic state to a hydrophilic swollen hydrogel state affecting the affinity of the cells to the substrate. As a result of this transition the patterned cell sheet will release from the substrate without breaking the interactions between the cells. Optionally, the patterned cell sheet may be treated with a releasing agent before the shape transition in order to facilitate the release.

The stimulus used to induce said shape transition is a thermal stimulus. At room temperature the responsive hydrogel shows strong swelling in water. In an incubator used for cell culture, however, a temperature of about 37° C. is maintained, which causes the hydrogel to collapse (PNIPAA has a lower critical solution temperature (LCST) at 33° C.).

It is yet to be noted that further embodiments which fall under the above description are described in the text.

Figure 4:
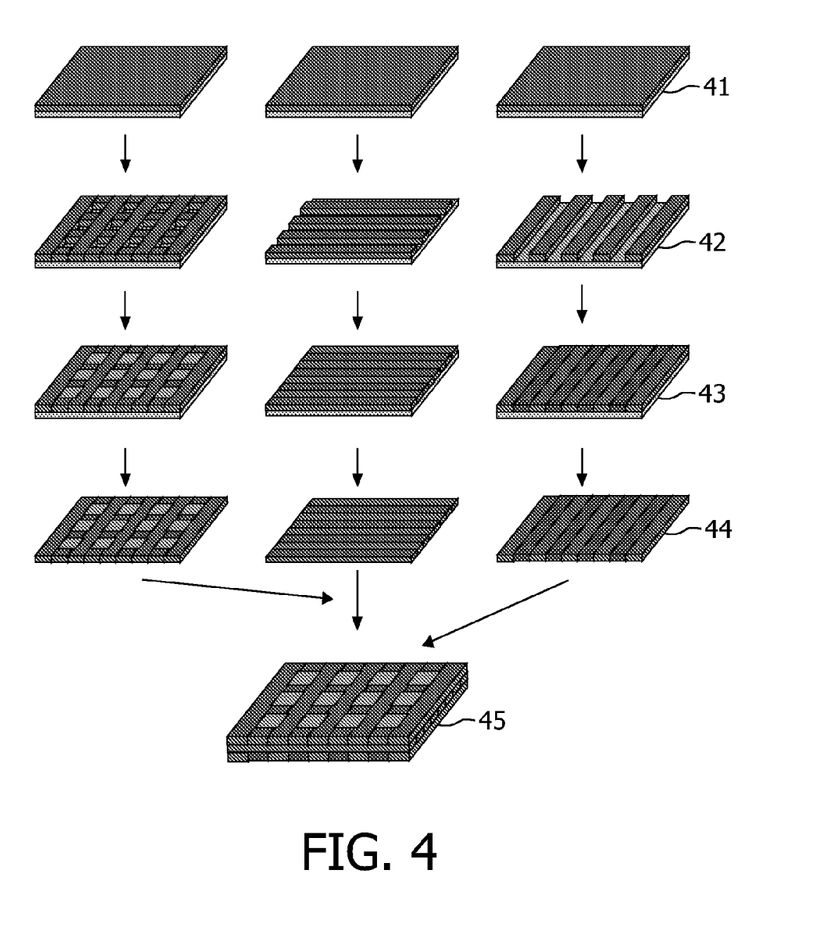
FIG. 4 shows a method for production of cell sheets comprising at least two different cell types.

FIG. 4 shows a method according to the present invention for the production of cell sheets comprising at least two different cell types, with steps 41-45. Step 41 demonstrates the step of growing a continuous cell sheet, preferably on a substrate comprising shape transition properties and/or alterable surface characteristics. Step 42 demonstrates a patterned "print and release step" as shown in FIG. 2. Note that in the three different columns, different patterns have been produced. Step 43 demonstrates a repopulation step with a second cell type. Step 44 demonstrates a release step of the thus produced heterogeneous cell sheet, as shown in FIG. 3. For this step, the shape transition properties and/or alterable surface characteristics of the substrate are important (see description). Step 45 demonstrates a step of stacking the different heterogeneous cell sheets thus produced in order to form a heterogeneous tissue or patch. Such patch can for example be used for the production of ocular surface tissues, periodontal ligaments, cardiac patches, bladder tissue, two-dimensional tissues, three-dimensional tissues, bone material, skin and/or cartilage material.

Note that other than shown in FIG. 4, the patch can as well consist of either two or more than three heterogeneous cell sheets.

In this context it is to be mentioned that in preferred embodiments of the present invention,

- the thickness of the substrate comprising shape transition properties and/or alterable surface characteristics, preferably the hydrogel layer, is in the range of $\geq 5$ nm and $\leq 50$ μm.
- the thickness of the substrate is, in case the substrate comprising shape transition properties and/or alterable surface characteristics is PNiPAA, in the range of $\geq 5$ nm and $\leq 50$ μm, more preferable in the range of $\geq 5$ nm and $\leq 50$ nm.
- The area of the cell sheets is in the range of $\geq 1$ cm$^2$ and $\leq 500$ cm$^2$.
- in case the stimulus for the induction of a shape transition in the substrate comprising shape transition properties and/or the alteration of surface characteristics is a temperature stimulus ($\Delta T$), such stimulus is in the range of $\geq 0.05$ and $\leq 5°$ C., preferably $\leq 2°$ C.
- the cell patterns produced have intervals, cell gaps and the like with a width and/or distance in the range of $\geq 3$ μm and $\leq 20$ mm,
- the instruments for the creation of the cell patterns, e.g. the stamp, comprise etching patterns with grids, intervals, gaps and the like with a width and/or distance in the range of $\geq 3$ μm and $\leq 20$ mm.

The invention claimed is:

1. A method for the production of cell sheets comprising at least two different cell types, said method comprising the steps of:
   a) providing a continuous cell sheet which is disposed on a substrate comprising shape transition properties and/or alterable surface characteristics;
   b) exposing said continuous cell sheet to a releasing agent in a patterned fashion;
   c) washing the cell sheet after exposure to the releasing agent in order to remove cells which have been affected by the releasing agent;
   d) repopulating the gaps remaining after the cells which have been affected by the releasing agent have been removed with a second cell type; and
   e) releasing the thus obtained cell sheet by inducing a shape transition in the said substrate without reducing a temperature of the medium.

2. The method according to claim 1, further comprising at least one repetition of steps b)-d).

3. The method according to claim 1, wherein said releasing agent is a chemical agent, an enzyme, or a physical stimulus, or any combination of these.

4. The method according to claim 1, wherein said releasing agent is loaded on a stamp having a relief structure which corresponds to the cell pattern to be produced.

5. The method according to claim 1, wherein the said releasing agent is administered to the cells in a patterned fashion by means of a plotter.

6. The method according to claim 1, wherein the said substrate comprising shape transition properties is a hydrogel.

7. The method according to claim 1, wherein the induction of a shape transition in the substrate comprising shape transition properties and/or the alteration of surface characteristics in the substrate comprising alterable surface characteristics comprises at least one of raising or lowering the osmolarity of the medium, raising or lowering the pH of the medium, and providing an electrical stimulus to the medium.

* * * * *